US008641725B2

(12) United States Patent
Celik

(10) Patent No.: US 8,641,725 B2
(45) Date of Patent: Feb. 4, 2014

(54) COMPRESSED AIR DISSECTOR (AIR JET SCRAPER)

(75) Inventor: Bulent Celik, Ankara (TR)

(73) Assignee: Tubitak, Ankara (TR)

( * ) Notice: Subject to any disclaimer, the term of this patent is extended or adjusted under 35 U.S.C. 154(b) by 283 days.

(21) Appl. No.: 12/293,145

(22) PCT Filed: Feb. 20, 2007

(86) PCT No.: PCT/TR2007/000016
§ 371 (c)(1),
(2), (4) Date: Apr. 10, 2009

(87) PCT Pub. No.: WO2007/106053
PCT Pub. Date: Sep. 20, 2007

(65) Prior Publication Data
US 2009/0326547 A1    Dec. 31, 2009

(30) Foreign Application Priority Data

Mar. 16, 2006  (TR) .............................. a 2006 01204

(51) Int. Cl.
*A61B 17/3203*    (2006.01)
(52) U.S. Cl.
USPC ........................................................ 606/115
(58) Field of Classification Search
USPC ............. 606/167, 115; 604/19, 22, 23, 24, 26
See application file for complete search history.

(56) References Cited

U.S. PATENT DOCUMENTS

| 4,316,462 A * | 2/1982 | Baker ........................... 604/190 |
| 4,357,940 A | 11/1982 | Muller |
| 5,536,242 A | 7/1996 | Willard et al. |
| 6,117,150 A * | 9/2000 | Pingleton et al. ............. 606/167 |
| 6,562,050 B1 * | 5/2003 | Owen ........................... 606/131 |
| 6,764,493 B1 * | 7/2004 | Weber et al. ................... 606/131 |
| 2002/0177802 A1 | 11/2002 | Moutafis et al. |
| 2005/0252352 A1 | 11/2005 | Tateiwa |

FOREIGN PATENT DOCUMENTS

| GB | 2112298 A | 7/1983 |
| WO | 99/02089 A | 1/1999 |

* cited by examiner

*Primary Examiner* — Ryan Severson
*Assistant Examiner* — Anh Dang
(74) *Attorney, Agent, or Firm* — Venable, Campillo, Logan & Meaney PC

(57) ABSTRACT

Compressed air dissector is a surgical dissector which is used in tumor dissection and excision phases in surgical branches and especially in neurosurgery and microsurgery. The problem at this point is removal of the tumoral tissue without damaging the adjacent normal tissue and the blood vessels feeding the normal tissue. Moreover, serious difficulties may be encounter in the dissection phase of the arachnoid matter in brain surgery. The occurring adhesions can easily be opened with the aid of the air dissector. This provides great convenience in aneurism surgery. The operation principle of the compressed air dissector is direction of the controlled, sterile compressed air (gas) to the brain parenchyma and removal of the dissected particles from the location with an aspirator system. In said system, the particles in the air are cleaned with a filter system. When the compressed air is directed to the tumor tissue it easily dissects and removes the tumor. In the meanwhile, as no liquids are present in the lacuna the operation site can be seen clearly. Furthermore, event the smallest vessels are protected. Thus, peroperative bleeding occurs less and the postoperative wound curing becomes more physiologic. Moreover, tissue damage due to thermal effect is out of the question during the use of compressed air dissector.

18 Claims, 2 Drawing Sheets

COMPRESSED AIR DISSECTOR (AIR JET SCRAPER)

FIELD OF THE INVENTION

Technical Field

Subject invention is related with compressed air dissector used in brain surgery and micro-surgery, and consists of scraping of the tumor, fat and similar particles with air and aspiration of said particles.

BACKGROUND

Known Status of the Technique

Various tools are used in dissection and removal of all kinds of lesions (glyome, metastatic tumors, menengioma, epilepsy surgery etc.) inside the cranium in brain surgery. These are mainly dissectors, bipolar, tumor forceps and aspirators. In line with the recent developments in technology, new generation of tools have been developed to assist removal of existing lesions with minimal damage to the normal brain tissue. Ultrasonic surgery aspirator (CUSA) and water jet dissector are examples of new generation tools.

The operation principle of CUSA consists of cutting of the tumor tissue with ultrasonic waves and aspiration of the particles. In the similar manner, the operation principle of the water jet dissector consists of provision of compressed water output from a small opening at a range of −150 bars, orientation of the compressed water on the tumor tissue on the brain to cut and scrape the tumor tissue and to remove the particles dissected from the tumor tissue and to remove these from the operation site with an aspirator.

Water jet dissector was first used by Papachristou and Barters as a surgical instrument in 1982. With said dissector which was used in liver surgery, the tissue was approached with compressed water and consequently determined that parenchymal tissue was dissected but the bile ducts and blood vessels were not damaged. Subsequently, water jet dissector was used in kidney, bone, vascular and craniomaxillofacial surgery, dermatology and ophthalmology. Tersiz et al. realized first experimental works in neurosurgery in 1989 and have demonstrated on a cadaver brain that dissection could be realized without damaging vessels greater than 20 micrometer. Good results have been achieved in meningiomas and metastatic brain tumors by application of a water jet of appropriate pressure on the tissue with a water jet dissector and suitable nozzle. In water jet dissector scraping method, water pressure and the dissection depth are increased in direct proportion and it has been determined vessels are protected in water jet values under 20 bars in said system. Thus, bleeding during the operation and edema at the surgery site in the postoperative period is reduced compared to other dissection methods while the surgery time is shortened, the tissues other than those to be scraped are damaged less and thus the surgery provides more effective results in terms of the patient. Just as so, water jet dissector is sued in a successful manner in metastatic brain tumors and meningiomas today.

One of the other important difficulties of brain surgery is prevention, reduction and control of bleeding during dissection. Limitation of the field of sight by the bleeding during operation makes reduction and control of the bleeding necessary. For this reason, surgery equipment that assists the blunt dissection of brain tumors is being developed. Ultrasonic surgery aspirators may be shown as examples of the developed equipment. Ultrasonic surgery aspirators are used in removal of tumors of medium hardness. Main disadvantage of this aspirator is that the hand applicator (tool) has a bulky and non-bending structure along with expensiveness of the tools. Moreover, the problem of limited field of sight in water jet dissectors as a result of the liquid applied to the medium is encountered in ultrasonic surgery aspirators also as a result of application to the surgery site serum physiologically.

As it is the case in some other laser applications, monopolar and bipolar coagulation methods are used in controlling the bleeding in the surgery by burning the cut and damaged vessels at the surgery site. However, it has been determined that these lead to adjacent tissue damage due to the thermal effect.

In addition to the fact that subject Air Jet Dissector has all of the positive features of the water jet dissector, it has been determined that more effective results are obtained in terms of bleeding control, precision at the operation site, clearness of the field of sight and sensitivity towards the adjacent tissues, compared to the disadvantages of other devices used generally in surgical dissection.

In the U.S. Pat. No. 4,357,940, titled Tissue Pneumatic Separator Structure, only application of compressed gas to the tissue and application of tissue dissection have been explained. Use of said tissue pneumatic separator is not possible in brain surgery and microsurgery procedures due to the fact that the handpiece is driven with compressed air. Said tool may lead to death or permanent disability of the patient as it shall cause undesired tissue damage in the brain during operation. The subject product of the invention uses sterile air in order to reduce the risk of postoperative infection, which is different to that of the above invention. Moreover, cutter function and removal of the cut tissues by aspiration are realized in addition to the tissue dissection.

U.S. Pat. No. 4,709,697, titled Tissue Pneumatic Separator Structure and Method, refers to a complicated handpiece. Said handpiece can only be used in rougher dissections. It does not include the aspiration function and the tissue cutting features. It can only be used in the dissection of coarse tissues due to the blunt end of the handpiece.

Patent no. WO 9902089, titled Pneumatic Tissue Dissector with Exhaust System, explains a system, which is used during laparoscopy in general surgery in enclosure inside the abdomen, that vacuums the gas applied from the other side in order to prevent the tension of the abdomen. The objective of said system is to ensure tissue separation by keeping the pressure inside the abdomen stable. In the subject system of the invention, 0-15 bar compressed air is applied to the air brain tissue and thus tissue dissection is realized to the tumor parts are cut. The cut parts are removed from the site with an aspirator system. Moreover, gradual increment of the compressed air is planned digitally and air pressure may be increased at 0.01 bar at each step. Thus, greater reliability is obtained in terms of control of the air directed to the brain. This is important in terms of protection of the smallest vessels that supply the brain, which is very significant in brain surgery.

U.S. Pat. No. 6,066,150, titled Surgical Dissection Instrument using a High-Pressure Liquid Jet, defines a system with a handpiece which realizes tissue dissection with a compressed water jet from the nozzle with aspiration feature, and which can be used with one hand and which provides rough adjustment of the compressed air. The most important disadvantage of the system is application of the serum physiologically as it is the case in the water jet dissector. Another disadvantage of this and similar systems is that they have failed to provide a solution for opening arachnoid adhesions in aneurism surgeries, which hold a significant place in brain surgery. Different to the above system, in the subject system of the invention, the field of view is clearer as no fluids are applied to the lacuna when compressed sterile air is applied to the brain and the surgeon is able to realize the operation in a more controlled manner, free of risks. Moreover, the arachnoid adhesions can easily be opened by application of compressed air into the arachnoid.

In Patent No. EP 0411170, titled Water Jet cutter and Aspirator for Brain Surgery, liquid is applied to the lacuna, similar to that of U.S. Pat. No. 6,066,150. The system defined in said patent can only be used in tissue cutting processes. It cannot be used in arachnoid dissection. In the system of the current invention, the field of view is clearer as sterile air is applied to the brain instead of a fluid and no fluids are applied, and the surgeon is able to realize the operation in a more controlled manner, free of risks. Moreover, the arachnoid adhesions can easily be opened by application of compressed air into the arachnoid. Furthermore, it can be used reliably since the degree of air applied to the brain can be increased or decreased in small pressure steps (±0.01 bars).

In addition to those defined in all of the patents, different tissue cutters and aspirators are present regarding the known aspects of the technique.

CUSA (Ultrasonic Surgical Aspirator): In the tests that have been conducted, it has been determined that CUSA damaged normal healthy tissue on the brain along with the targeted tissue during operation. Accordingly, CUSA is not able to provide the required and desired results in terms of protection small blood vessels. Moreover, absence of the arachnoid dissection feature restricts the use of this system in brain surgery greatly.

Laser knife: The researches revealed that this system causes local heat increments and undesired tissue damages along the incision line. Moreover, the necessity of special glasses worn by the operation team prevents use of this system in sensitive operations like bran and micro surgery.

Electrical Knife: The researches revealed that the Electrical Knife lead to local heat increments like the laser knife. Therefore, there is the potential of causing tissue damage due to heat increment in undesired sections. Along with all of the above negative aspects in terms of brain surgery, the heavy, bulky structure of the handpiece restricts the area of use substantially.

SUMMARY

Figure 1:
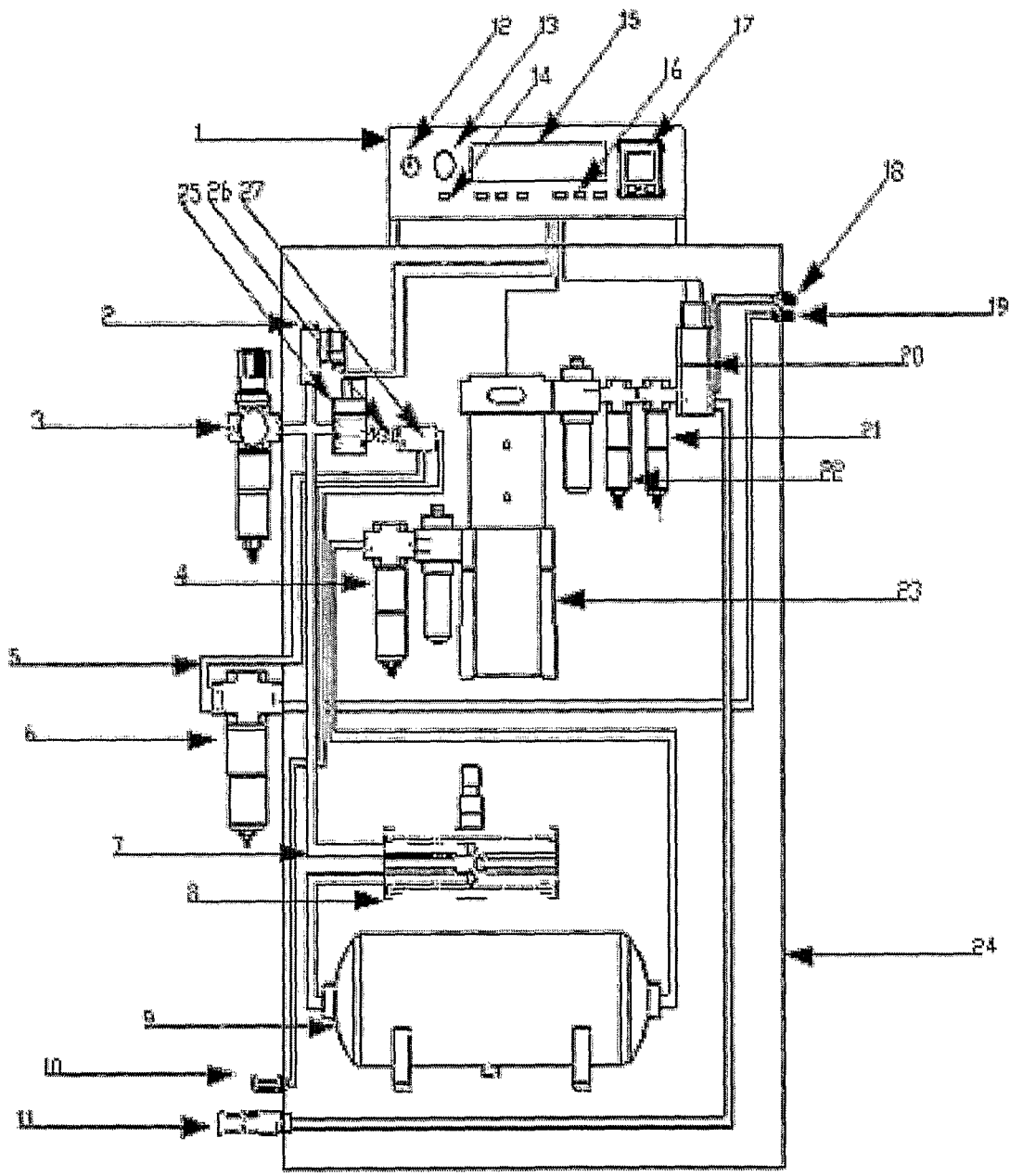
FIG. 1 is one preferred embodiment of a controlling system providing compressed air and vacuum and a control cabin.

Effects and Advantages of Use of Microsurgery Compressed Air Scraper in Brain Surgery The system explained in the current invention, demonstrates rather reliable features in microsurgery operations compared with other systems. Operation of the system in 0-15 bar range and digital increment of the compressed air are planned, and the possibility of a 0.01 bar increment of air pressure at each step is the main component that provides precise execution of the operation. Thus, control of the air directed to the brain is much safer. Secondly, sterility of the air used in the operation, which is being provided from within the system and the system having a developed air sterilization system for said purpose is another distinctive characteristic. As the system operates with sterile air with adjustable pressure, it is possible to use it as both a dissector and a cutter in the brain, and scraping and cutting features can also be used, as required, with different end-pieces thanks to the removable tip of the handpiece. The integration of the aspiration system, which provides for removal of the tissues cut during the operation and blood etc. unwanted particles that block the view and which operates simultaneously with the cutting and scraping process, is one of the basic features that differentiates the current invention from the others. On the contrary to the those in previous systems, the field of view and control of the surgeon is improved by a fluid not being applied to the surgery lacuna. Absence of the thermal effect, which leads to tissue damage in Laser Knife, electrical knife and monopolar and bipolar coagulation, minimizes the damage on regions other than the targeted tissue and on the blood vessels, and thus the postoperative tissue curing becomes more physiological.

Morphologically and microscopically significant changes occur in the brain tissue in the peroperative and postoperative period as a result of use of all of said instruments, based on the known issues of the above technique. However, effectiveness and side effects of use of said instruments vary greatly. Said changes which occur on the tissue in the peroperative and postoperative period, play an important role in terms of each surgical instrument gaining an advantaged or disadvantaged position over one another.

Technical Problems the Invention Aims to Solve

Use of compressed jet air in the dissection and resection of the mass lesion in the brain has advantages over other methods. This invention, which can be used in the dissection of the tumoral tissue especially during tumor operations in brain surgery, does not damage the blood vessels of the normal brain tissue, does not have a thermal impact as the working temperature and the jet air temperature are equal to room temperature and provides a better view of the area as no liquids are applied to the lacuna during the operation. Moreover, sterile air is used. Thus, the possibility of postoperative infection is reduced significantly. As the pressure increment precession is 0.01 bar, it can be used safely in brain surgery and microsurgery. Postoperative bleeding occurs significantly less and thus the postoperative glial scar tissue formation is decreased.

DETAILED DESCRIPTION OF THE INVENTION

The operation principle of the air jet dissector is direction of compressed air on to the brain parenchyma and removal of the dissected parts with the aid of an aspirator system. It consists of three main units. These are the control cabin (FIG. 1), compressed air unit and the tool (handpiece), (FIGS. 2-39.

Air from the compressor passes through a 40 micron filter and regulator (3). Its function is to clean the particles in the air line up to 40 microns, and to regulate input pressure of the device. Compressed air passing through the filter-regulator enters the system from the bacteria-free air line (7).

The system pressure at system input is branched into 3. First branch extends to the pressure switch (2) and an electrical signal is sent to the control cabin to protect the system against high pressure. The second branch extends to the pressure booster (8). Its function is to boost the pressure entering the system to 15 bars to obtain the operation pressure. The third branch is to produce the vacuum required for aspiration.

The increased pressure from the booster is forwarded to an air tank (9). The function of the air tank is to store the pressure and prevent the pressure fluctuations that may occur in the system. The compressed air from the air tank is forwarded to the filter group. First, it passes through a 5 micron compressed air filter (4). The objective is to prevent easy clogging of the subsequent microfilters. From there, the air enters the air drier unit (23) where the water and oil particles in the air are removed. The air exiting the air drier unit is filtered through 0.1 micron filter (22) and 0.001 micron filter (21) for removal of the bacteria and viruses that may be present in the compressed air line to provide sterile air for use in the operation. The air subjected to said processes shall have sterilization better than 1.2.1 class based on ISO norms.

Air prepared for the operation shall enter the proportionate pressure regulator (20). The proportionate pressure regulator shall be controlled with a microprocessor at the control cabin (1). The flow and pressure amount of the compressed air to be used during the operation shall be controlled by the surgeon thanks to said eleetropneumatic regulator. Said sterile air shall be transferred to the input handpiece (tool) (18).

Vacuum required for aspiration shall be created by the vacuum unit integrated into this device. Compressed air shall pass through the eleetropneumatic valve (25) and shall either switch the vacuum on or off based on the signal from the aspirator on/off button on the control cabin. The flow of the air passing through said valve shall be regulated with the messages, which are controlled with the aspirator flow regulation button (13) located at the control cabin and which are sent to the flow regulator valve (26). Air with regulated flow enters the vacuum generator (27) to produce the vacuum. From the vacuum line (5) it is forwarded to the vacuum filter (6). From there it is fed to the aspirator (19) input.

The digital display (15) on the control cabin displays the system status. Menu buttons (14) under the display provide certain possibilities to the surgeon in line with the software written on to the microprocessor. These are pressure increment, pressure reduction, pressure on-off and storage of the required pressure values. The digital pressure indicator displays the pressure applied in the operation in bar or psi units. Thus, the surgeon is able to adjust the pressure to be applied much more reliably and the applied pressure is displayed on the screen.

The pressure of the compressed air, entering from the compressed air input (32) at the handle of the unit of the subject invention and moving along the cylindrical space in the handle, shall be controlled through the buttons (35) designed to be placed on the handle, as required, with a connection (36) connected to the control cabin, and thus the operation shall be realized free of interruptions by a single surgeon. Sterile air moving along the cylindrical spaced in the handle with pressure regulated from the buttons on the handle, shall be jetted at required thickness to the operation area with a single tip, which can be mounted to the handle with changeable diameter or one of the tips (28) of different diameters. The targeted tissue particles that are scraped or dissected with the jet air are removed with the aspiration tip (30), integrated to the handle, and sent to the vacuum filter (6). A button is considered to be placed on the handle to switch the vacuum on and off or to regulate the vacuum power.

Tests related with the invention: Total of 32 New Zealand male rabbits (2.4-3.2 kg) were grouped in 4 groups with 8 in each. Intraperitoneal 50 mg/kg ketamin HCL and 5 mg/kg rompun were mixed for use as anesthetics. Following the bifrontal skin incision, frontolateral craniotomy was performed and dura under the bone defect were opened. Subsequently, frontal corticotomy was realized with the compressed air dissector on the left frontal hemisphere and with CUSA to the right hemisphere. Animals were killed by administration of intraperitoneal pentotal on the first, third, seventh days and on the sixth week depending on their groups, and morphological and immunohistopathologic changes on the 2 frontal lobes were evaluated. Peroperative bleeding amount, protection of blood vessels, postoperative brain edema, intracranial hemorrhage width and amount, dissection depth and dissection border quality, astroglia and microglia reaction breakdown were evaluated.

Animals were killed as follows:
Group 1: 1 day after
Group 2: 3 days after
Group 3: 7 days after
Group 4: 6 weeks after
and the changes occurring on the frontal lobes were examined. (Groups were determined with consideration of the surgical wound curing phases.)
Method:
The parameters selected for examination are as follows:
Peroperative bleeding amount
Postoperative brain edema
Intracranial hemorrhage width and amount
Dissection depth and dissection border quality
Astroglia and microglia reaction breakdown Peroperative bleeding amount: Evaluation of the bleeding at the areas were corticotomy was performed with CUSA and compressed air dissector revealed that the bleeding on the left hemisphere which was subjected to compressed air dissector was substantially less.

Bleeding that filled the whole site was observed in the right hemisphere, which was subjected to corticotomy with CUSA. Normal brain tissue could not be seen before the lacuna was aspirated. Only the dissected, normal brain parenchyma was observed at the side which was operated with the air jet dissector. Bleeding was substantially less compared to CUSA.

Postoperative brain edema: After killing of the animals, the brain edema was documented independently by three difference brain surgery research assistants (semi-quantitatively). Accordingly;
0: no edema at the operation site.
1: macroscopic perifocal edema exists.
2: severe perifocal edema present in addition to the herniation to the exterior of the craniotomy.

Scoring was realized accordingly and statistically meaningful differences in terms of brain edema in the postoperative were investigated with the ki square test.

Table 1: As a result of the comparison of CUSA and the Air-Jet dissector based on the evaluation of the left/right lobes of the brains of all animals, notwithstanding their respective groups, in terms of edema (with the ki square test), it has been observed that postoperative edema was statistically higher on the right lobe where CUSA was used ($p=0.0002$).

TABLE 1

General: Lobe/Edema dual tabulation

| Lobe/Edema | | | Edema | | | | Total |
|---|---|---|---|---|---|---|---|
| | | | 0 | 1 | 2 | 3 | |
| Lobe | Left lob | Number | 14 | 16 | 0 | 0 | 30 |
| | | % in the lobe | 46.7% | 53.3% | 0.0% | 0.0% | 100.0% |
| | Right lob | Number | 3 | 15 | 10 | 2 | 30 |
| | | % in the lobe | %10.0 | 50.0% | 33.3% | 6.7% | 100.0% |
| Total | | Number | 17 | 31 | 10 | 2 | 60 |
| | | % in the lobe | 28.3% | 51.7% | 16.7% | 3.3% | 100.0% | p = 0.0002

Table 2: As a result of the comparison of CUSA and Air-Jet dissector based on the evaluation of the left/right lobes in terms of edema with due consideration of groups, it has been observed that postoperative edema was statistically meaningful on the right lobe where CUSA was used in groups 1 and 2. (p1=0.004, p2–0.00001)

TABLE 2

Lobe edema tabulation by groups

| Group | Group/Lobe/Edema | | | Edema | | | | Total |
|---|---|---|---|---|---|---|---|---|
| | | | | 0 | 1 | 2 | 3 | |
| Group 1 (postop day 1.) | Lobe | Left Lobe | Number | 4 | 4 | 0 | 0 | 8 |
| | | | % in the lobe | 50.0% | 50.0% | 0.0% | 0.05 | 100.0% |
| | | Right Lobe | Number | 0 | 4 | 4 | 0 | 8 |
| | | | % in the lobe | 0.0% | 50.0% | 50.0% | 0.0% | 100.0% |
| | Total | | Number | 4 | 8 | 4 | 0 | 16 |
| | | | % in the lobe | 25.0% | 50.0% | 25.0% | 0.0% | 100.0% |
| Group 1 (postop day 3.) | Lobe | Left Lobe | Number | 0 | 8 | 0 | 0 | 8 |
| | | | % in the lobe | 0.0% | 100.0% | 0.0% | 0.0% | 100.0% |
| | | Right Lobe | Number | 0 | 0 | 6 | 2 | 8 |
| | | | % in the lobe | 0.0% | 0.0% | 75.0% | 25.0% | 100.0% |
| | Total | | Number | 0 | 8 | 6 | 2 | 16 |
| | | | % in the lobe | 0.0% | 50.0% | 37.5% | 12.5% | 100.0% |
| Group 3 (postop week 1.) | Lobe | Left Lobe | Number | 3 | 4 | 0 | 0 | 7 |
| | | | % in the lobe | 42.9% | 57.1% | 0.0% | 0.0% | 100.0% |
| | | Right Lobe | Number | 1 | 6 | 0 | 0 | 7 |
| | | | % in the lobe | 14.3% | 85.7% | 0.0% | 0.0% | 100.0% |
| | Total | | Number | 4 | 10 | 0 | 0 | 14 |
| | | | % in the lobe | 28.6% | 71.4% | 0.0% | 0.0% | 100.0% |
| Group 4 (postop 6$^{th}$ week) | Lobe | Left Lobe | Number | 7 | 0 | 0 | 0 | 7 |
| | | | % in the lobe | 100.0% | 0.0% | 0.0% | 0.0% | 100.0% |
| | | Right Lobe | Number | 2 | 5 | 0 | 0 | 7 |
| | | | % in the lobe | 28.6% | 71.4% | 0.0% | 0.0% | 100.0% |
| | Total | | Number | 9 | 5 | 0 | 0 | 14 |
| | | | % in the lobe | 64.3% | 35.7% | 0.0% | 0.0% | 100.0% | p values:
Group 1: 0.004
Group 2: 0.00001
Group 3: 0.559
Group 4: 0.021

Intracranial hemorrhage width and amount: The width of the bleeding at the operation site was evaluated semi-quantitatively again.

0: bo blood at the dissection area.

1: blood filling the dissection area present.

2: subdural or epidural extensive blood present.

Said results have been evaluated with ki square test and the one with the least bleeding at the operation lacuna has been observed. Moreover, the intracranial bleeding amount has been evaluated (quantitatively) at microscopic levels with morphometric methods on days 1, 3 and 7. Thus, the vascular damage amounts due to surgical trauma have been determined in a clearer manner. (The width and amount of intracranial hemorrhage were evaluated in all postoperative wound curing phases.)

Table 3: As a result of the comparison of CUSA and the Air-Jet dissector based on the evaluation of the left/right lobes of the brains of all animals, notwithstanding their respective groups, in terms of hemorrhage (with the Id square test), it has been observed that postoperative hemorrhage was statistically higher on the right lobe where CUSA was used (p=0.002).

TABLE 3

General: Lobe/Hemorrhage dual tabulation

| Lobe/Hemorrhage | | | Hemorrhage | | | Total |
|---|---|---|---|---|---|---|
| | | | 0 | 1 | 2 | |
| Lobe | Left Lobe | Number | 14 | 15 | 1 | 30 |
| | | % in the lobe | 46.7% | 50.0% | 3.3% | 100.0% |

TABLE 3-continued

General: Lobe/Hemorrhage dual tabulation

| Lobe/Hemorrhage | | Hemorrhage | | | Total |
|---|---|---|---|---|---|
| | | 0 | 1 | 2 | |
| | Right Number | 4 | 16 | 10 | 30 |
| | Lobe % in the lobe | 13.3% | 53.3% | 33.3% | 100.0% |
| Total | Number | 18 | 31 | 11 | 60 |
| | % in the lobe | 30.0% | 51.7% | 18.3% | 100.0% | p = 0.002

Table 4: As a result of the comparison of CUSA and Air-Jet dissector based on the evaluation of the left/right lobes in terms of hemorrhage with due consideration of groups, it has been observed that postoperative hemorrhage was statistically meaningful on the right lobe where CUSA was used in groups 1 and 2. (p1=0.015, p2=0.013)

TABLE 4

Lobe/Hemorrhage by Groups

| Group | Group/Lobe/Hemorrhage | | | Hemorrhage | | | Total |
|---|---|---|---|---|---|---|---|
| | | | | 0 | 1 | 2 | |
| Group 1 | Lobe | Left | Number | 4 | 3 | 1 | 8 |
| (postop day 1) | | Lobe | % in the lobe | 50.0% | 37.5% | 12.5% | 100.0% |
| | | Right | Number | 0 | 3 | 5 | 8 |
| | | Lobe | % in the lobe | 0.0% | 37.5% | 62.5% | 100.0% |
| | Total | | Number | 4 | 6 | 6 | 16 |
| | | | % in the lobe | 25.0% | 37.5% | 37.5% | 100.0% |
| Group 1 | Lobe | Left | Number | 2 | 6 | 0 | 8 |
| (postop day 3) | | Lobe | % in the lobe | 25.0% | 75.0% | 0.0% | 100.0% |
| | | Right | Number | 0 | 4 | 4 | 8 |
| | | Lobe | % in the lobe | 0.0% | 50.0% | 50.0% | 100.0% |
| | Total | | Number | 2 | 10 | 4 | 16 |
| | | | % in the lobe | 12.5% | 62.5% | 25.0% | 100.0% |
| Group 3 | Lobe | Left | Number | 2 | 5 | 0 | 7 |
| (postop week 1) | | Lobe | % in the lobe | 28.6% | 71.4% | 0.0% | 100.0% |
| | | Right | Number | 0 | 6 | 1 | 7 |
| | | Lobe | % in the lobe | 0.0% | 85.7% | 14.3% | 100.0% |
| | Total | | Number | 2 | 11 | 1 | 14 |
| | | | % in the lobe | 14.3% | 78.6% | 7.1% | 100.0% |
| Group 4 | Lobe | Left | Number | 6 | 1 | 0 | 7 |
| (postop week 6) | | Lobe | % in the lobe | 85.7% | 14.3% | %0.0% | %100.0% |
| | | Right | Number | 4 | 3 | 0 | 7 |
| | | Lobe | % in the lobe | 51.7% | 42.9% | 0.0% | 100.0% |
| | Total | | Number | 10 | 4 | 0 | 14 |
| | | | % in the lobe | 71.4% | 28.6% | 0.0% | 100.0% | p values:
Group 1: 0.015
Group 2: 0.013
Group 3: 0.119
Group 4: 0.554

Dissection depth and dissection border quality: Observation of the surgery shall be recorded peroperatively. Moreover, the sections taken from the dissection areas have been stained with hematoxylin & eosin dyes and the tissue losses compatible with the dissection areas in the preparations shall be examined and interpreted.

Astroglia and microglia reaction breakdown: To be evaluated with immunohistologic analysis. Standard GPAF dye shall be used for astroglia distinction and MCA (monoclonal mouse antibody) or CD-68 stain shall be used for microglia-macrophage distinction. The device causing greater rate of granulation tissue on the brain in the post-operative late period (week 1-week 6) shall be determined with this method. Thus, the surgical traumas of the devices can be evaluated and compared.

FORM OF APPLICATION OF THE INVENTION IN INDUSTRY

Subject work is an air-jet dissector that functions with a compressed air and aspirator system, which has been planned and devised for use in the surgery of intracranial tumors in neurosurgery with priority, which can also be used in microsurgery. As it is known, dissection is of the essence in surgery. Although it is primarily planned for use in neurosurgery, it is a very significant equipment that can be used in the dissection of the mass tissue in all surgery sections.

FIGURES

FIG. 1: Controlling system providing compressed air and vacuum, control cabin

Figure 2:
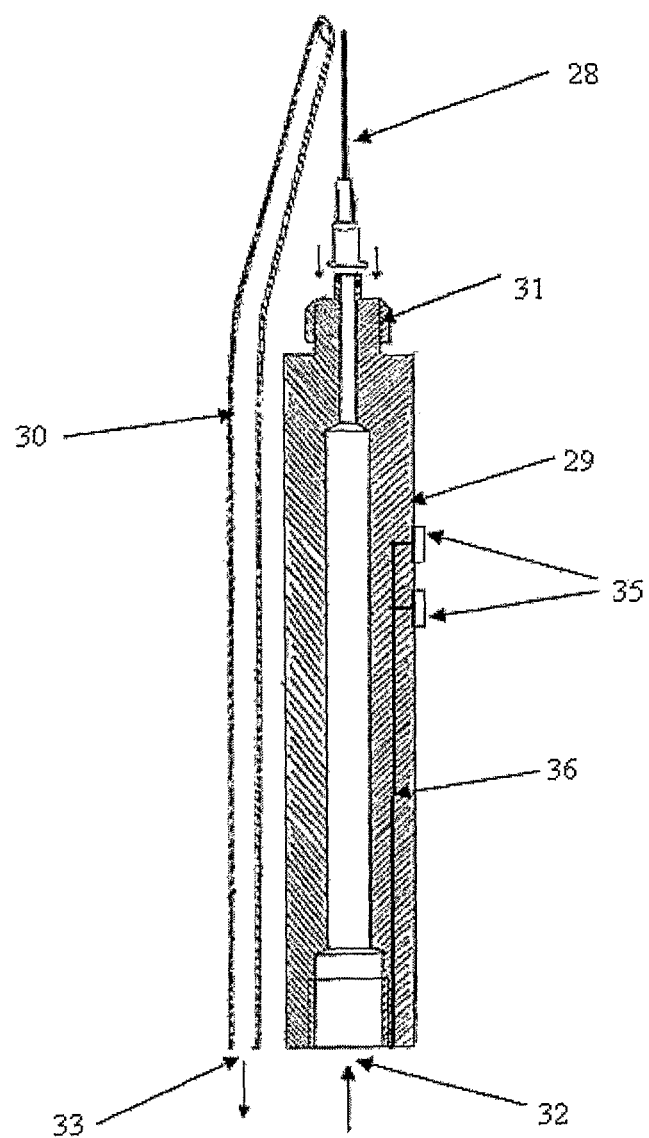
FIG. 2 is one preferred embodiment of a handle, aspirator and a cutter/scraper apparatus on which a jet tip is located.
Figure 3:
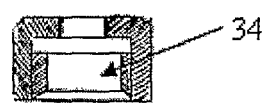
FIG. 3 is one preferred embodiment of a jet nozzle fastening/adjustment flap.

FIG. 2: Handle, aspirator and the cutter/scraper apparatus on which the jet tip is located FIG. 3: Jet nozzle fastening/adjustment flap

PART NUMBERS GIVEN IN THE FIGURES

1. Control Panel
2. Pressure Switch
3. 40 µm Air Fitter Regulator
4. 5 µm Air Filter
5. Vacuum line
6. Vacuum filter
7. Pressure line
8. Booster, Pressure booster
9. Compressed air tank
10. Vacuum exhaust
11. Pressure exhaust
12. Device on/off button 13. Aspirator flow adjustment
14. Aspirator on/off
15. Digital display
16. Menu buttons
17. Digital pressure key
18. Compressed air output/tool input
19. Aspirator input
20. Proportionate pressure regulator
21. 0.01 μm Air Filter
22. 0.1 μm Air Filter
23. Air drier unit
24. Device cabin and frame
25. Electro-pneumatic valve
26. Flow regulation valve
27. Vacuum generator
28. Shaped jet nozzle
29. Apparatus body, handle
30. Aspirator tip
31. Jet nozzle fastening flap input
32. Compressed air input
33. Output of dissected parts and air
34. Jet nozzle fastening flap
35. Pressure amount control buttons
36. Control cabin connection

The invention claimed is:

1. A system for scraping of tumors, fat, lesions and similar particles, separation of tissues and aspiration of the dissected or cut particles in micro surgery, comprising:
   a. a control cabin having a digital pressure display, a microprocessor for controlling pressure values and for storing the required pressure values in a memory, an aspiration flow regulation button, and an aspiration on/off button;
   b. a compressed air unit to compress air and having a filter-regulator unit, a bacteria free air line, a pressure booster, an air tank, at least two air filter systems for filtering particles of different sizes sufficient for removal to below the size of bacteria and/or virus particles, an air drier unit, an electropneumatic proportional pressure regulator, and a vacuum unit for aspiration;
   c. an operation apparatus having a handle for transferring the compressed air having removed particles to below the size of bacteria and/or virus particles to a jet nozzle, the jet nozzle having a changeable diameter or multiple interchangeable jet nozzle tips with fixed diameters, a jet nozzle fastener flap for mounting of the jet nozzle to the handle or changing the diameter of the mounted nozzle, buttons on the handle for changing the pressure amount from the control cabin wherein the buttons being integrated to the handle wherein the compressed air having been removed from particles to below the size of bacteria particles is jetted from the jet nozzle tip.

2. A system according to claim 1, wherein the two systems of the compressed air unit comprise a 1-20 micron air filter system and a 0-0.2 micron air filter system.

3. A system according to claim 2, wherein the vacuum unit of the compressed air unit comprises an electropneumatic valve, a flow regulation valve, a vacuum generator and a vacuum filter.

4. A system according to claim 2, wherein the pressure booster is capable of increasing the pressure entering the system from 0 up to 15 bars.

5. A system according to claim 4, wherein the vacuum unit of the compressed air unit comprises an electropneumatic valve, a flow regulation valve, a vacuum generator and a vacuum filter.

6. A system according to claim 2, wherein the filter regulator unit of the compressed air unit comprises a 20-60 micron filter.

7. A system according to claim 6, wherein the pressure booster is capable of increasing the pressure entering the system up to 15 bars.

8. A system according to claim 7, wherein the vacuum unit of the compressed air unit comprises an electropneumatic valve, a flow regulation valve, a vacuum generator and a vacuum filter.

9. A system according to claim 1, wherein the filter regulator unit of the compressed air unit comprises a 20-60 micron filter.

10. A system according to claim 9, wherein the vacuum unit of the compressed air unit comprises an electropneumatic valve, a flow regulation valve, a vacuum generator and a vacuum filter.

11. A system according to claim 9, wherein the pressure booster is capable of increasing the pressure entering the system up to 15 bars.

12. A system according to claim 11, wherein the vacuum unit of the compressed air unit comprises an electropneumatic valve, a flow regulation valve, a vacuum generator and a vacuum filter.

13. A system according to claim 1, wherein the pressure booster is capable of increasing the pressure entering the system up to 15 bars.

14. A system according to claim 13, wherein the vacuum unit of the compressed air unit comprises an electropneumatic valve, a flow regulation valve, a vacuum generator and a vacuum filter.

15. A system according to claim 1, wherein the vacuum unit of the compressed air unit comprises an electropneumatic valve, a flow regulation valve, a vacuum generator and a vacuum filter.

16. A system according to claim 1, wherein the at least two air filter systems for filtering particles of different sizes comprise a 0.1 micron filter and a 0.001 micron filter.

17. A system for scraping of tumors, fat, lesions and similar particles, separation of tissues and aspiration of the dissected or cut particles in micro surgery, comprising:
   a control cabin having a digital pressure display, a microprocessor for controlling pressure values and for storing the required pressure values in a memory, an aspiration flow regulation button, and an aspiration on/off button;
   a compressed air unit to compress air and remove particles to at least 1.2.1 class based on ISO norms having a filter-regulator unit, a bacteria free air line, a pressure booster, an air tank, at least two air filter systems for filtering particles of different sizes to provide sterilization, an air drier unit wherein water and oil particles are removed, an electropneumatic proportional pressure regulator, and a vacuum unit for aspiration;
   an operation apparatus having a handle for receiving the 1.2.1 class based on ISO norms compressed air and then transferring the 1.2.1 class based on ISO norms compressed air to a jet nozzle for jetting the 1.2.1 class based on ISO norms compressed air to an operational area, the jet nozzle having a changeable diameter or multiple interchangeable jet nozzle tips with fixed diameters, a jet nozzle fastener flap for mounting of the jet nozzle to the handle or changing the diameter of the mounted nozzle, buttons on the handle for changing the pressure amount from the control cabin wherein the buttons being integrated to the handle.

18. A system for scraping of tumors, fat, lesions and similar particles, separation of tissues and aspiration of the dissected or cut particles in micro surgery, comprising:
- a control cabin having a digital pressure display, a microprocessor for controlling pressure values and for storing the required pressure values in a memory, an aspiration flow regulation button, and an aspiration on/off button;
- a compressed air unit to compress air and having a filter-regulator unit, a bacteria free air line, a pressure booster to increase the compressed air to 15 bars, an air tank to store the compressed air at 15 bars, at least two air filter systems for filtering particles of different sizes sufficient for removal to below the size of bacteria and/or viruses particles, an air drier unit between the at least two air filter systems wherein water and oil particles are removed, an electropneumatic proportional pressure regulator, and a vacuum unit for aspiration;
- an operation apparatus used for micro surgery having a handle for transferring the compressed air having removed particles to below the size of bacteria and/or virus particles to a jet nozzle, the jet nozzle having a changeable diameter or multiple interchangeable jet nozzle tips with fixed diameters, a jet nozzle fastener flap for mounting of the jet nozzle to the handle or changing the diameter of the mounted nozzle, buttons on the handle for changing the pressure amount from the control cabin wherein the buttons being integrated to the handle.

* * * * *